US011123009B2

(12) United States Patent
Garcia Molina et al.

(10) Patent No.: US 11,123,009 B2
(45) Date of Patent: Sep. 21, 2021

(54) SLEEP STAGE PREDICTION AND INTERVENTION PREPARATION BASED THEREON

(71) Applicant: KONINKLIJKE PHILIPS N.V., Eindhoven (NL)

(72) Inventors: Gary Nelson Garcia Molina, Madison, WI (US); Erik Bresch, Eindhoven (NL); Ulf Grossekathöfer, Eindhoven (NL); Adrienne Heinrich, Den Bosch (NL); Sander Theodoor Pastoor, Vleuten (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 129 days.

(21) Appl. No.: 16/209,522

(22) Filed: Dec. 4, 2018

(65) Prior Publication Data
US 2019/0192069 A1    Jun. 27, 2019

Related U.S. Application Data

(60) Provisional application No. 62/608,646, filed on Dec. 21, 2017.

(51) Int. Cl.
*A61B 5/00* (2006.01)
*A61M 21/02* (2006.01)
(Continued)

(52) U.S. Cl.
CPC ............ *A61B 5/4812* (2013.01); *A61B 5/369* (2021.01); *A61M 21/02* (2013.01); *G16H 20/00* (2018.01);
(Continued)

(58) Field of Classification Search
CPC .............. A61M 21/02; A61M 2230/63; A61M 2205/3584; A61M 2021/0027;
(Continued)

(56) References Cited

U.S. PATENT DOCUMENTS

| 7,041,049 B1* | 5/2006 | Raniere ................. A61M 21/02 128/905 |
| 2004/0193068 A1* | 9/2004 | Burton ..................... A61B 5/11 600/544 |

(Continued)

FOREIGN PATENT DOCUMENTS

| WO | 2016087983 A1 | 6/2016 |
| WO | 2016089313 A1 | 6/2016 |

OTHER PUBLICATIONS

International Search Report and Written Opinion, International Application No. PCT/EP2018/086061, dated Apr. 23, 2019.
(Continued)

*Primary Examiner* — Navin Natnithithadha
*Assistant Examiner* — Sunita Reddy

(57) ABSTRACT

The present disclosure pertains to a system configured to facilitate prediction of a sleep stage and intervention preparation in advance of the sleep stage's occurrence. The system comprises sensors configured to be placed on a subject and to generate output signals conveying information related to brain activity of the subject; and processors configured to: determine a sample representing the output signals with respect to a first time period of a sleep session; provide the sample to a prediction model at a first time of the sleep session to predict a sleep stage of the subject occurring around a second time; determine intervention information based on the prediction of the sleep stage, the intervention information indicating one or more stimulator parameters related to periheral stimulation; and cause one or more
(Continued)

stimulators to provide the intervention to the subject around the second time of the sleep session.

18 Claims, 8 Drawing Sheets

(51) Int. Cl.
    *G16H 20/00*     (2018.01)
    *A61B 5/369*     (2021.01)

(52) U.S. Cl.
    CPC .......... *A61B 5/4809* (2013.01); *A61B 5/4815* (2013.01); *A61B 5/7275* (2013.01)

(58) Field of Classification Search
CPC ...... A61M 2210/06; A61M 2021/0044; A61M 2021/0055; A61M 2021/0072; A61M 2209/088; A61M 2230/10; A61M 2021/0016; A61M 2205/3561; A61M 2205/50; A61M 2230/40; A61M 2205/3553; A61M 2205/3592; A61M 2230/005; A61B 5/4812; A61B 5/7275; A61B 5/4815; A61B 5/0476; A61B 5/4809; G16H 20/00
USPC ..................................................... 600/26–28
See application file for complete search history.

(56) References Cited

U.S. PATENT DOCUMENTS

| | | | | |
|---|---|---|---|---|
| 2005/0076908 | A1* | 4/2005 | Lee | A61N 1/36514 128/204.23 |
| 2005/0283039 | A1* | 12/2005 | Cornel | A61M 21/02 600/27 |
| 2006/0106275 | A1* | 5/2006 | Raniere | A61M 21/02 600/26 |
| 2006/0293608 | A1* | 12/2006 | Rothman | A61B 5/4812 600/545 |
| 2007/0249952 | A1* | 10/2007 | Rubin | A61B 5/6814 600/544 |
| 2010/0087701 | A1* | 4/2010 | Berka | A61M 21/02 600/27 |
| 2011/0295083 | A1* | 12/2011 | Doelling | A61B 5/11 600/301 |
| 2013/0303837 | A1 | 11/2013 | Berka et al. | |
| 2014/0316192 | A1* | 10/2014 | de Zambotti | A61B 5/0205 600/28 |
| 2015/0190086 | A1 | 7/2015 | Chan et al. | |
| 2015/0224017 | A1* | 8/2015 | Graindorge | A61H 23/00 601/46 |
| 2017/0258398 | A1* | 9/2017 | Jackson | A61B 5/742 |

OTHER PUBLICATIONS

D. Antonenko, S. Diekelmann, C. Olsen, J. Born, and M. Mölle, "Napping to renew learning capacity: enhanced encoding after stimulation of sleep slow oscillations.," Eur. J. Neurosci., No. Feb. 2012, pp. 1-10, Jan. 2013.

M. Massimini, F. Ferrarelli, S. K. Esser, B. A. Riedner, R. Huber, M. Murphy, M. J. Peterson, and G. Tononi, "Triggering sleep slow waves by transcranial magnetic stimulation.," Proc. Natl. Acad. Sci. U. S. A., vol. 104, No. 20, pp. 8496-8501, May 2007.

B. A. Riedner, B. K. Hulse, F. Ferrarelli, S. Sarasso, and G. Tononi, "Enhancing sleep slow waves with natural stimuli," Medicamundi, vol. 45, No. 2, pp. 82-88, 2010.

J. D. Rudoy, J. L. Voss, C. E. Westerberg, and K. A. Paller, "Strengthening Individual Memories by Reactivating Them During Sleep," Science (80-. )., vol. 326, No. 5956, pp. 1079-1079, 2009.

J. W. Antony, E. W. Gobel, J. K. O'Hare, P. J. Reber, and K. A. Paller, "Cued memory reactivation during sleep influences skill learning," Nat. Neurosci., vol. 15, No. 8, pp. 1114-1116, 2012.

D. Oudiette, J. W. Antony, J. D. Creery, and K. A. Paller, "The Role of Memory Reactivation during Wakefulness and Sleep in Determining Which Memories Endure," J. Neurosci., vol. 33, No. 15, pp. 6672-6678, 2013.

X. Hu, J. W. Antony, J. D. Creery, I. M. Vargas, G. V. Bodenhausen, and K. A. Paller, "Unlearning implicit social biases during sleep," Science (80-. )., vol. 348, No. 6238, pp. 1013-1016, 2015.

H.-V. Ngo, A. Miedema, I. Faude, T. Martinetz, M. Molle, and J. Born, "Driving Sleep Slow Oscillations by Auditory Closed-Loop Stimulation—A Self-Limiting Process," J. Neurosci., vol. 35, No. 17, pp. 6630-6638, 2015.

M. Bellesi, B. A. Riedner, G. Garcia-Molina, C. Cirelli, and G. Tononi, "Enhancement of sleep slow waves: underlying mechanisms and practical consequences," Front. Syst. Neurosci., vol. 8, No. October, pp. 1-17, Oct. 2014.

O. Tsinalis, P. M. Matthews, Y. Guo, and S. Zafeiriou, "Automatic Sleep Stage Scoring with Single-Channel EEG Using Convolutional Neural Networks," 2016.

M. Längkvist, L. Karlsson, and A. Loutfi, "Sleep Stage Classification Using Unsupervised Feature Learning," Adv. Artif. Neural Syst., vol. 2012, pp. 1-9, 2012.

\* cited by examiner

SLEEP STAGE PREDICTION AND INTERVENTION PREPARATION BASED THEREON

CROSS-REFERENCE TO PRIOR APPLICATIONS

This application claims the benefit of U.S. Provisional Application No. 62/608,646, filed on 21 Dec. 2017. This application is hereby incorporated by reference herein.

BACKGROUND

Field

The present disclosure pertains to a system and method for facilitating prediction related to a sleep stage and/or intervention preparation in advance of the sleep stage's occurrence.

Description of the Related Art

Sleep monitoring and sleep stage detection systems are frequently used to identify sleep disorders or in connection with sleep therapy. Typical systems may provide subjects with sleep therapy by providing the subject with peripheral (e.g. sensory, electric or magnetic) simulation to a subject during sleep. However, such systems often apply sensory stimulation continuously to a subject during sleep without regard to the subject's current sleep stage and/or at intervals that do not correspond to the subject's sleep states. The present disclosure overcomes deficiencies in prior art systems.

SUMMARY

Accordingly, one or more aspects of the present disclosure relate to a system configured to facilitate prediction of a sleep stage and intervention preparation in advance of the sleep stage's occurrence. The system comprises one or more sensors configured to be placed on a subject and to generate output signals conveying information related to brain activity of the subject. The system comprises one or more physical processors configured by computer-readable instructions to: determine a sample representing the output signals with respect to a first time period of a sleep session; provide, during the sleep session, the sample to a prediction model at a first time of the sleep session to predict a sleep stage of the subject occurring around a second time of the sleep session; determine, prior to the second time, intervention information based on the prediction of the sleep stage, the intervention information indicating one or more stimulator parameters related to peripheral stimulation; and cause, based on the intervention information, one or more stimulators to provide the intervention to the subject around the second time of the sleep session.

Another aspect of the present disclosure relates to a method for facilitating prediction of a sleep stage and intervention preparation in advance of the sleep stage's occurrence, the method comprising: generating, with one or more sensors, output signals conveying information related to brain activity of a subject; determining, the one or more physical processors, a sample representing the output signals with respect to a first time period of a sleep session; providing, with the one or more physical processors, during the sleep session, the sample to a prediction model at a first time of the sleep session to predict a sleep stage of the subject occurring around a second time of the sleep session; determining, with the one or more physical processors, prior to the second time, intervention information based on the prediction of the sleep stage, the intervention information indicating one or more stimulator parameters related to peripheral stimulation; and causing, with the one or more physical processors, based on the intervention information, one or more stimulators to provide the intervention to the subject around the second time of the sleep session.

Still another aspect of the present disclosure relates to a system configured to facilitate prediction of a sleep stage and intervention preparation in advance of the sleep stage's occurrence. The system comprises means for generating output signals conveying information related to brain activity of the subject; and means for determining a sample representing the output signals with respect to a first time period of a sleep session; means for providing, during the sleep session, the sample to a prediction model at a first time of the sleep session to predict a sleep stage of the subject occurring around a second time of the sleep session; means for determining, prior to the second time, intervention information based on the prediction of the sleep stage, the intervention information indicating one or more stimulator parameters related to peripheral stimulation; and means for causing, based on the intervention information, one or more stimulators to provide the intervention to the subject around the second time of the sleep session.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
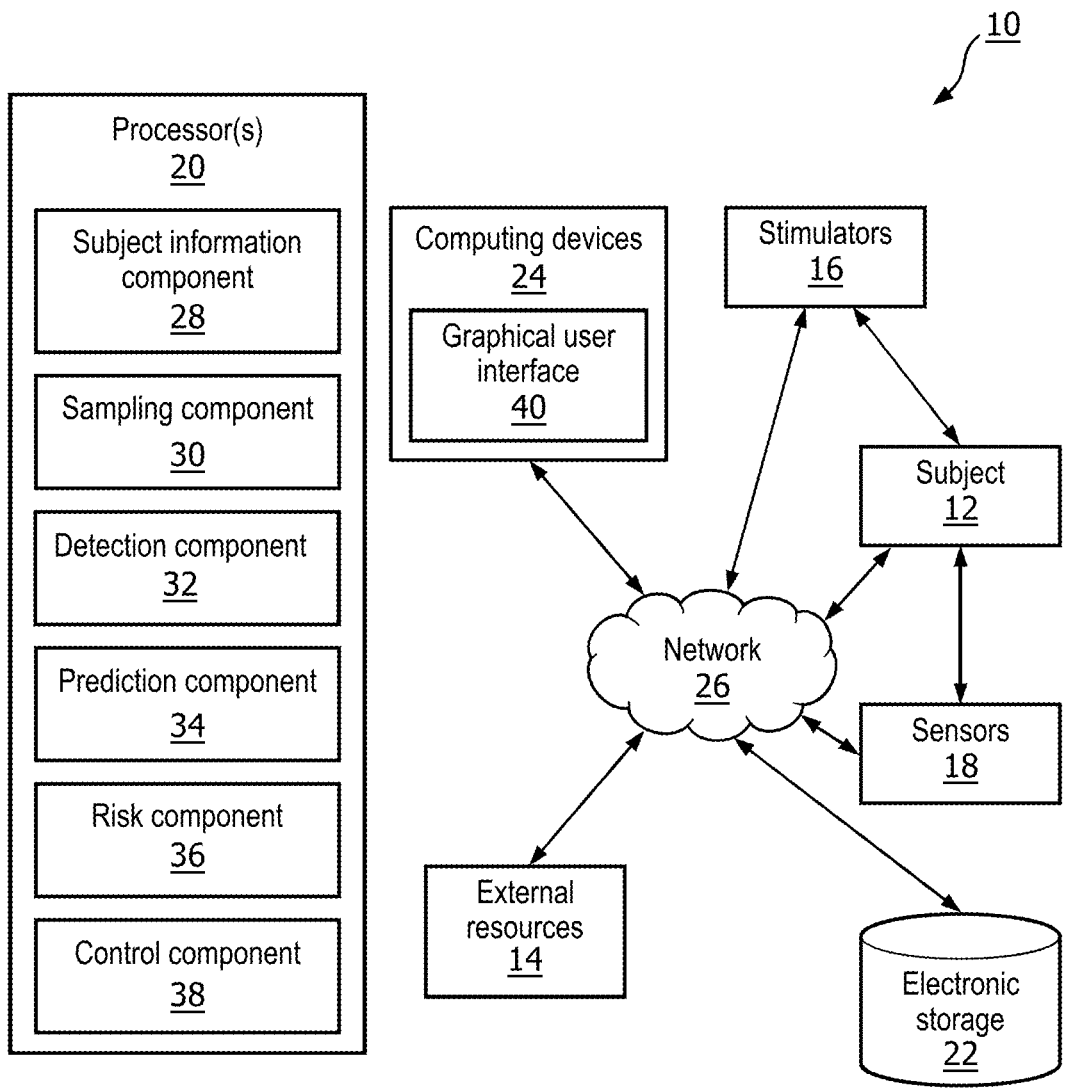
FIG. 1 is a schematic illustration of a system configured to facilitate prediction related to sleep states and/or intervention preparation in advance of the sleep stage's occurrence, in accordance with one or more embodiments.

As used herein, the singular form of "a," "an," and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Intervention during sleep (e.g., peripheral stimulation) may have several cognitive and therapeutic benefits that enhance sleep quality, increase the restorative value of sleep, and strengthen cognitive functions. In general, stimulation during sleep try to modify sleep brain activity (e.g., via peripheral stimulation) without changing the overall sleep architecture or cause sleep disturbance. To accomplish this, closed-loop reactive strategies are adopted which modify the nature of the intervention in response to changes in the sleep state. Optimization of the intervention and enhancement of the effect requires proactive strategies that predict, in real-time, future sleep state transitions.

Figure 2:
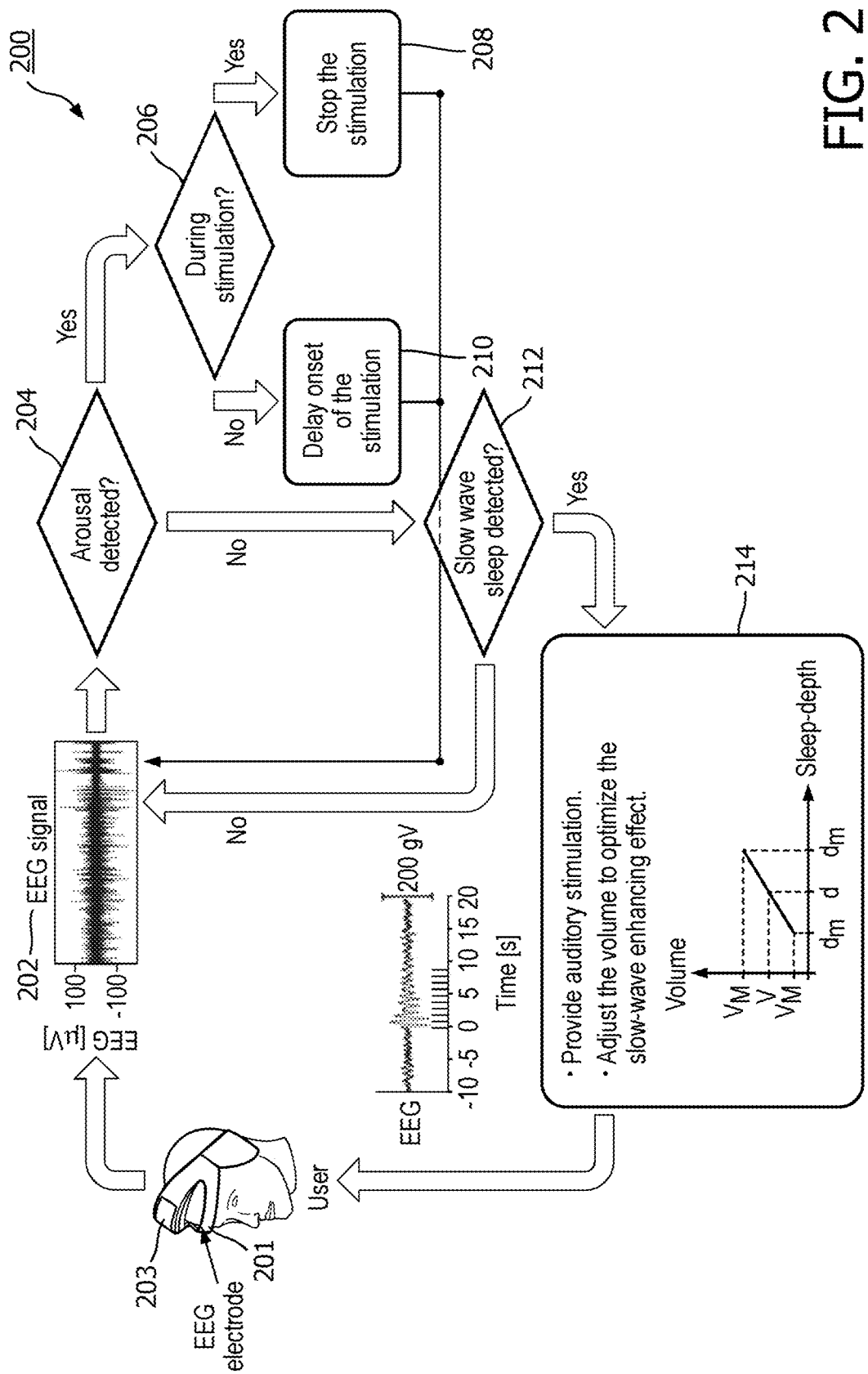
FIG. 2 illustrates example operations performed by a system configured to detect sleep states, in accordance with one or more embodiments.

FIG. 2 illustrates example operations performed by system 200 configured to detect sleep states in real time. In some embodiments, system 200 may include wearable device 201, which may include one or more sensors, processors, stimulators, or other components. In this example, system 200 is an electroencephalogram (EEG) based system that detects deep sleep in real-time and delivers auditory stimulation to enhance sleep slow waves without causing arousals. Wearable device 201 includes sensory stimulator 203 (which is an auditory stimulator in this case). Arousal (e.g., sleep micro-arousals) in subject 12 may be detected using EEG signals 202. Arousals are high frequency events that can be observable in the EEG signals 202, which indicate that the subject is waking up. Detecting arousals may be achieved by calculating the EEG power in the alpha (8-12 Hz) and beta (15-30 Hz) frequency bands and comparing them to pre-established thresholds. The presence of an arousal delays the onset of the next auditory stimulation. Ongoing stimulation stops if an arousal is detected. If no arousal is detected, then the system attempts to detect N3 (slow wave) sleep by calculating EEG power in the 0.5 to 4 Hz frequency band (slow wave activity or SWA), and quantifying the density of slow waves. If the duration of detected N3 sleep is at least 1.5 minutes, and sleep depth (ratio between delta and beta powers) exceeds a pre-established threshold then auditory stimulation is delivered. This can be seen in FIG. 2, if no arousal 204 is detected, and a slow wave 212 is detected, sensory stimulator 203 provides auditory stimulation to subject 12. Auditory stimulation consists of 50-millisecond long tones separated from each other by a fixed 1-second long inter-tone interval. The volume of each tone is modulated by sleep depth such that loud (soft) tones are played during deeper (shallower) sleep. Adjusting the volume of the auditory stimulation enhances the slow wave effect 214. If arousal 204 is detected in subject 12 during stimulation period 206, stimulator 203 stops stimulation 208. If the arousal 204 is detected outside the stimulation period 206, the sensory stimulator delays the auditory stimulation 210. These approaches (described in FIG. 2) to intervene during sleep are reactive in nature because the decision to intervene (e.g. stimulation in a specific sleep stage) is taken within few seconds (between 100 milliseconds to 5 seconds) of the intervention. The general approach toward intervention is to do so in a manner that sleep architecture or sleep duration is not affected. This indicates the need for a more proactive strategy.

System 10 (described in FIG. 1) may allow for sleep signals that are currently monitored to be utilized along with the history of sleep dynamics to predict future sleep stages with a prediction horizon that is longer than few seconds (e.g. >10 seconds). This may allow for a more accurate intervention time, and may allow for preparation of the intervention (type of stimulations, time interval between the stimulations, intensity of the stimulations, volume of the stimulations, frequency, and/or other parameters of the sensory intervention) before occurrence of the sleep state. Predicting sleep states with more accuracy may allow for better energy management and life extension (e.g., of stimulators and/or one or more components of the system) because the intervention is not continuous (occurs only when the appropriate sleep state is predicted).

In some embodiments, system 10 comprises one or more of stimulator(s) 16, sensor(s) 18, a processor 20, electronic storage 22, client computing platform(s) 24, a network 26, and/or other components. In FIG. 1, stimulator(s) 16, sensor(s) 18, processor 20, electronic storage 22, and client computing platform(s) 24 are shown as separate entities. In some embodiments, some and/or all of the components of system 10 and/or other components may be grouped into one or more singular devices (e.g., a wearable device or other user device). In some embodiments, a wearable device may include a housing, one or more sensors (e.g., sensors 18), processors (e.g., processors 20), stimulators (e.g., stimulators 16), or other components. In some embodiments, the wearable device may be configured to include one or more sensors, one or more processors, and one or more sensor stimulators within the housing. In some embodiments, the wearable device may be configured to include one or more sensors and one or more processors within the housing and one or more sensor stimulators outside of the housing. In some embodiments, the wearable device may be configured to include one or more processors and one or more sensor stimulators within the housing and one or more sensors outside of the housing. Such sensors, processors, stimulators, and other components of the wearable device, whether housed within or outside of the housing, may communicate with one another via wired or wireless connections. It should be noted that, although some embodiments are described herein with respect to a wearable device performing certain operations, one or more such operations may be performed by one or more other components (e.g., one or more servers, client devices, etc.). As an example, such other components (e.g., one or more servers, client devices, etc.) may include one or more processor components that are the same as or similar to subsystems components 28-38.

Figure 3:
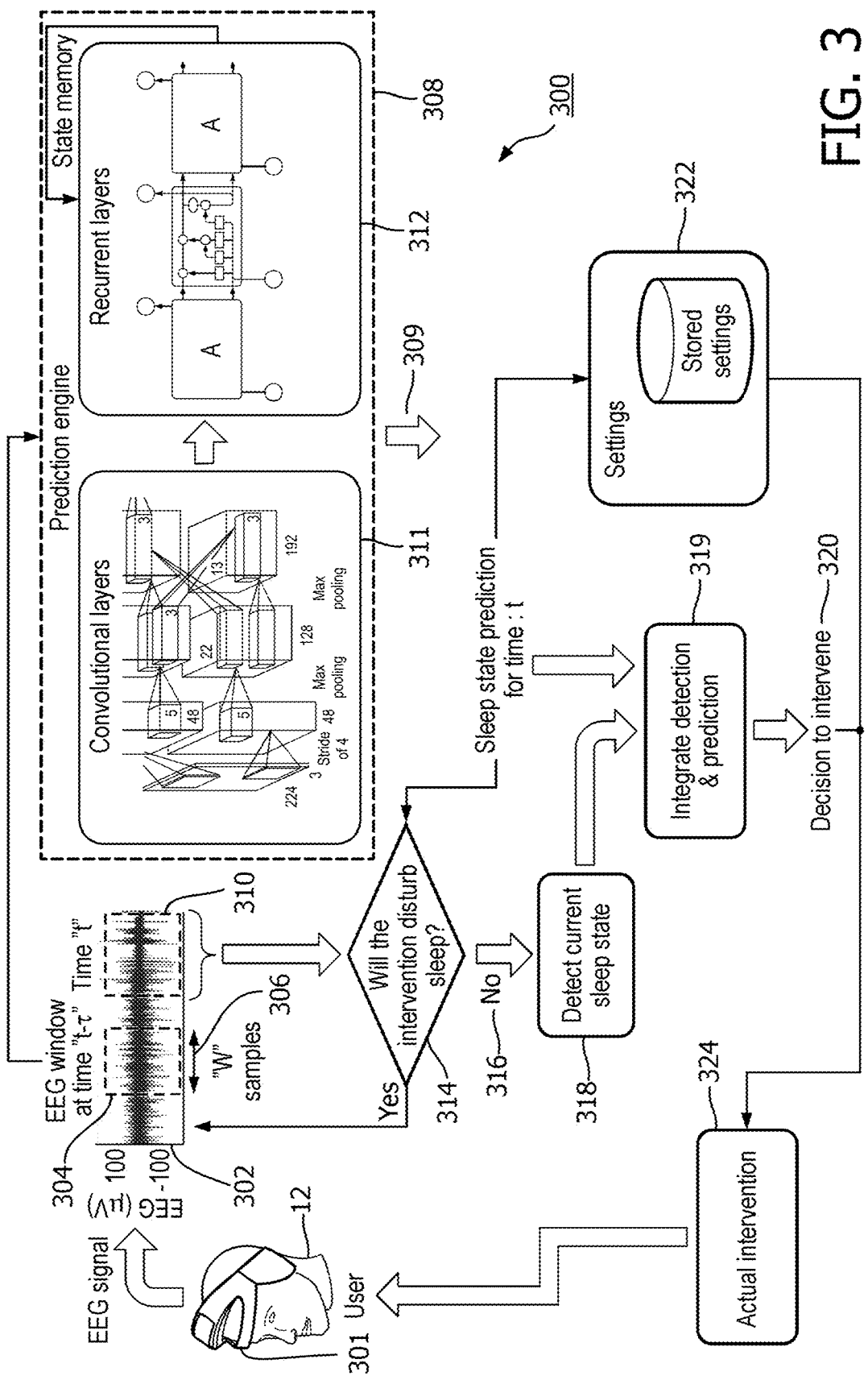
FIG. 3 illustrates example operations performed by a system configured to predict sleep states, in accordance with one or more embodiments.

The wearable device may be any device that is worn, or that is in full or partial contact with any body parts of the subject. FIG. 3 (described below) shows an example of a wearable device that may be in the form of a headband 301. In some embodiments, headband may include sensing electrodes, a reference electrode located behind the ear of subject, one or more devices associated with an EEG, a wireless audio device, and one or more audio speakers located in and/or near the ears of subject and/or in other locations. The sensing electrodes may be configured to generate output signals conveying information related to brain activity of subject. The output signals may be transmitted to a computing device (within or outside of the wearable device) wirelessly and/or via wires. For example, in some embodiments, system 10 of FIG. 1 may be similar to wearable device 301 of FIG. 3 or may be included in a wearable device similar to wearable device 301 of FIG. 3. In some embodiments, some or all components of system 10 of FIG. 1 may be included in a wearable device similar to wearable device 301 of FIG. 3.

Returning to FIG. 1, stimulator(s) 16 is configured to provide stimulation to subject 12. In some embodiments, stimulation provided to the subject may be peripheral stimulation (e.g., sensory, electric, magnetic, etc.). In some embodiments, other types of stimulation may be considered. Stimulator(s) 16 may be configured to provide stimulation to subject 12 prior to a sleep session, during a current sleep session, after a sleep session, and/or at other times. In some embodiments, stimulation comprises auditory stimulation, light stimulation, electrical stimulation, haptic stimulation, magnetic stimulation, visual stimulation, and/or olfactory stimulation. For example, stimulator(s) 16 may be configured to provide stimulation to subject 12 during slow wave sleep in a sleep session. Stimulator(s) 16 may be configured to provide stimulation to subject 12 during a sleep session to induce sleep slow waves and/or enhance sleep slow waves in subject 12. In some embodiments, stimulator(s) 16 may be configured to induce and/or enhance sleep slow waves through non-invasive brain stimulation and/or other methods. Stimulator(s) 16 may be configured to induce and/or enhance sleep slow waves through non-invasive brain stimulation using stimulation including odors, sounds, visual stimulation, touches, tastes, and/or other stimulation. In some embodiments, stimulator (s) 16 may be configured to induce and/or enhance sleep slow waves via auditory stimulation of subject 12. Examples of stimulator(s) 16 may include one or more of a music player, a tone generator, a collection of electrodes on the scalp of subject 12, a unit to deliver vibratory stimulation (also known as somato-sensory stimulation), a coil generating a magnetic field to directly stimulate the brain's cortex, light generators, a fragrance dispenser, and/or other stimulators.

In some embodiments, transcranial direct current stimulation (TDCS) and transcranial alternate current stimulation (TACS), in which a device sends a small current across the scalp to modulate brain function, may be used. These types of stimulators may have beneficial effects for sleep with sustained after-effect after the stimulation. The slowly oscillating stimulation may induce an immediate increase in slow wave sleep, endogenous cortical slow oscillations, and slow spindle activity in the frontal cortex. In some embodiments, delivery of TDCS and TACS is targeted specifically in non-REM after detection/prediction of sleep stage 2 to induce an immediate increase in slow wave sleep.

In some embodiments, transcranial magnetic stimulation (TMS) delivered during deep NREM sleep may trigger slow waves and enhance sleep depth. In some embodiments, a stimulation (e.g., auditory, haptic, olfactory or visual) may be used to target memory reactivation during sleep. In some embodiments, by associating a sound cue while learning to perform a specific task, the cue may be replayed while the subject is sleeping to strengthen their memory of that task. The cues may be more effective if played in a specific sleep cycle (e.g., the slow-wave phase).

In some embodiments, type of stimulations, time interval between the stimulations, intensity of the stimulations, volume of the stimulations, frequency, and/or other parameters of the stimulator(s) may be adjusted by input from users, subjects, one or more component within or outside of system 10. Adjustments to one or more parameters (e.g., type of stimulation, time interval, intensity, volume, frequency, etc.) of the stimulator(s) may be based on information from individual subjects, information from individual users (e.g., healthcare professionals, caregivers, etc.), individual therapies, manufacturer settings, and/or other information. For example, one or more characteristics (or parameters) of the sensory stimulations (e.g., type of stimulation, time interval, intensity, volume, frequency, etc.) may be adjusted between upper and lower thresholds. The upper and lower thresholds for the characteristics may be determined for each subject based on previous tests (or may be based on similarities between subjects). For example, to set the upper threshold for a given subject, the subject may be presented with progressively increasing stimulation and asked to estimate a level of stimulation the subject thinks can wake him up. In other examples, characteristics of the stimulation may be tested on the subject during one or more sleep session to determine the upper and lower thresholds of the stimulation that will the lowest risk of sleep disturbance. In some embodiments, the characteristics of the stimulation (e.g., upper and lower thresholds) may be set based on response of one or more other subjects to the stimulations. The one or more subjects may have one or more similarities with the subject (e.g., brain activity, demographic information, vital sign information, medical/health condition information, treatment history information, similar desired outcome, and/or other similarities.

Sensor(s) 18 is configured to generate output signals conveying information related to brain activity of subject 12. The brain activity of subject 12 may correspond to sleep states and/or other characteristics of subject 12. Sleep states may include, correspond to, and/or be indicative of sleep stages. The brain activity of subject 12 may be associated with sleep states and/or sleep stages that include, correspond to, and/or be indicative of rapid eye movement (REM) sleep, non-rapid eye movement (NREM) sleep (e.g., slow wave sleep), and/or other sleep states. Sensor(s) 18 may comprise one or more sensors that measure such parameters directly. For example, sensor(s) 18 may include electrodes configured to detect electrical activity along the scalp of subject 12 resulting from current flows within the brain of subject 12. Sensor(s) 18 may comprise one or more sensors that generate output signals conveying information related to brain activity of subject 12 indirectly. For example, one or more sensors 18 may generate an output based on a heart rate of subject 12 (e.g., sensor(s) 18 may be a heart rate sensor located on the chest of subject 12, and/or be configured as a bracelet on a wrist of subject 12, and/or be located on another limb of subject 12), movement of subject 12 (e.g., sensor(s) 18 may include a movement detector placed on the subject body, bracelet around the wrist and/or ankle of subject 12 with an accelerometer such that sleep may be analyzed using actigraphy signals, a camera, a light movement detector, and/or other movement detectors), respiration of subject 12, and/or other characteristics of subject 12. Although sensor(s) 18 is illustrated at a single location near subject 12, this is not intended to be limiting. Sensor(s) 18 may include sensors disposed in a plurality of locations, such as for example, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), and/or in other locations.

In some embodiments, sensor(s) 18 may include some or all parts of positron-emission tomography (PET) equipment, magnetoencephalography (MEG) equipment, functional MRI equipment, functional near-infrared spectroscopy equipment, single-photon emission computed tomography equipment, and/or other devices/equipment configured to detect brain activity.

Processor 20 is configured to provide information processing capabilities in system 10. As such, processor 20 may include one or more of a digital processor, an analog processor, and a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may include a plurality of processing units. These processing units may be physically located within the same device (e.g., a server), or processor 20 may represent processing functionality of a plurality of devices operating in coordination (e.g., one or more servers, one or more computing devices 24 associated with users, a medical device, stimulator(s) 16, sensor(s) 18, a piece of a hospital equipment, devices that are part of external resources 14, electronic storage 22, and/or other devices.)

As shown in FIG. 1, processor 20 is configured to execute one or more computer program components. The one or more computer program components may comprise one or more of a subject information component 28, a sampling component 30, a detection component 32, a prediction component 34, a risk component 36, a control component 38, and/or other components. Processor 20 may be configured to execute components 28, 30, 32, 34, 36, 38 and/or other components by software; hardware; firmware; some combination of software, hardware, and/or firmware; and/or other mechanisms for configuring processing capabilities on processor 20.

It should be appreciated that although components 28, 30, 32, 34, 36, and 38 are illustrated in FIG. 1 as being co-located within a single processing unit, in embodiments in which processor 20 comprises multiple processing units, one or more of components 28, 30, 32, 34, 36, 38, and/or other components may be located remotely from the other components. The description of the functionality provided by the different components 28, 30, 32, 34, 36, 38 and/or other components described below is for illustrative purposes, and is not intended to be limiting, as any of components 28, 30, 32, 34, 36, and/or 38 may provide more or less functionality than is described. For example, one or more of components 28, 30, 32, 34, 36, and/or 38 may be eliminated, and some or all of its functionality may be provided by other components 28, 30, 32, 34, 36, and/or 38. As another example, processor 20 may be configured to execute one or more additional components that may perform some or all of the functionality attributed below to one of components 28, 30, 32, 34, 36, and/or 38.

Subject information component 28, in some embodiments, may be configured to determine (and/or obtain) information related to subject 12. In some embodiments, subject information component 28 may be configured to determine information related to brain activity of the subject based on output signals from sensor(s) 18. As described above, the brain activity information may include the subject's sleep states information. In some embodiments, information related to subject 12 may include biographical information. For example, biographical information may include demographic information (e.g., gender, ethnicity, age, etc.), vital sign information (e.g., heart rate, temperature, respiration rate, weight, BMI, etc.), medical/health condition information (e.g., a disease type, severity of the disease, stage of the disease, categorization of the disease, symptoms, behaviors, readmission, relapse, etc.), treatment history information (e.g., type of treatments, length of treatment, current and past medications, etc.), and/or other information. In some embodiments, subject information component 28 may include information related to sleep and/or brain activity information (e.g., previous sleep studies, previous brain activity information, previous sleep states information, and/or other sleep and brain activity related information.)

In some embodiments, subject information component 28 may be configured to determine (and/or obtain) information related to other subjects. For example, subjects with similar brain activity information, demographic information, vital sign information, medical/health condition information, treatment history information, similar desired outcome (e.g., from sensory simulation), similar sleep information, and/or other similarities with subject 12. It should be noted that the subject information described above is not intended to be limiting. A large number of information related to subjects may exist and may be used with system 10 in accordance with some embodiments. For example, users may choose to customize system 10 and include any type of subject data they deem relevant.

In some embodiments, subject information component 28 may be configured to obtain/extract information from one or more databases (e.g., included in electronic storage 22, external resources 14, one or more medical devices, other internal or external databases, and/or other sources of information). In some embodiments, different databases may contain different information about subject 12. In some embodiments, some databases may be associated with specific subject information (e.g., a medical condition, a demographic characteristic, a treatment, a therapy, a medical device used, a vital sign information, etc.) or associated with a set of subject information (e.g., a set of medical conditions, a set of demographic characteristics, a set of treatments, a set of therapies, a set of medical devices used, a set of vital signs information, etc.). In some embodiments, subject information component 28 may be configured to obtain/extract the subject information from external resources 14 (e.g., one or more external databases included in external resources 14), electronic storage 22 included in system 10, one or more medical devices, and/or other sources of information.

Sampling component 30 may be configured to determine (and/or receive) a sample representing the output signals with respect to a given time period of a sleep session. For example, sampling component may be configured samples of the output signals sampled by one or more components of system 10. In some embodiments, sampling components 30 may be configured to sample the received output signals from sensors 18. The samples of output signals may correspond to different time periods during the sleep session. The time periods may be of any lengths (e.g., lengths may range from milli-seconds to minutes). In some embodiments, sampling components 30 may be configured to sample the output signals continuously during parts of (or the whole) sleep session. In some embodiments, samples of the output signals may be consecutive, may overlap, may be periodic, may be random, or may be any other type of samples. In some embodiments, sampling component 30 may be configured to sample the output signals in a raw format (e.g., directly as received from the sensor(s)). In some embodiments, sampling component 30 may be configured to generate a representation of the output signals before generating the samples. For example, sampling component 30 may be configured to generate a representation of the output signals in the frequency domain before generating the samples. In some embodiments, representation of the output signals may be in the form of 2D or 3D images, and or other representations of the output signals.

Detection component 32 may be configured to detect sleep states and/or sleep stages in subject 12. In some embodiments, detection component 32 may be configured to detect sleep states (and/or sleep stages) based on the output signals from sensor(s) 18, and/or based on other information received from other components within or outside of system 10. In some embodiments, sleep states of subject 12 may correspond to one or more of wakefulness, REM sleep, stage N1, stage N2, and/or stage N3 sleep, and or other sleep states. In some embodiments, the individual sleep stages include a deep sleep stage. In some embodiments, deep sleep, slow wave sleep, and/or slow wave activity may correspond to stage N3 sleep. In some embodiments, stage N2 and/or stage N3 sleep may be deep sleep and/or slow wave sleep and/or may correspond to deep sleep and/or slow wave activity. In some embodiments, detection component 32 is configured such that detecting individual sleep stages includes selecting a sleep stage from the set of potential sleep stages (e.g., wakefulness, REM, N1, N2, N3), wherein the set of potential sleep stages includes the deep sleep stage.

In some embodiments, detection component module 32 may determine the current sleep stage of subject 12 based on an analysis of the information conveyed by the output signals of sensor(s) 18. The analysis may include generating and/or monitoring a representation of the output signals during parts or the entire sleep session. For example, analysis may include generating and/or monitoring an EEG during the sleep session of subject 12. In some embodiments, the analysis may include detecting slow wave sleep based on a power in a delta band and/or a power in a beta band of the EEG, and/or other information.

In some embodiments, prediction component 34 may be configured to predict a sleep state of the subject. For example, in some embodiments, prediction component 34 may receive a sample from sampling component 30 at a first time during a given sleep period of the sleep session. The sample represents output signals indicating brain activity of the subject during the first time. Prediction component 34 may be configured to predict a sleep state of the subject that may occur around a second time (during the same sleep period or a different sleep period of the sleep session). In some embodiments, the second time may be in the order of a milli-second, one second, two seconds, five seconds, ten seconds, one minute, two minutes, five minutes, or other amount of time after the first time. In some embodiments, the second time may be between 1 ms and hours after the first time.

In some embodiments, prediction component 34 is configured to predict one or more (future) sleep states based on previously detected sleep states (e.g., by detection module 30). In some embodiments, prediction component 34 may be configured to predict deep sleep and/or slow wave occurrence within the sleep states. In some embodiments, prediction component 34 may be configured to predict one or more sleep stated based on previous sleep and/or brain activity information. For example, prediction component 34 may be configured to predict one or more sleep states for the second time based on the sleep states detected from the sample provided to the prediction model at the first time. In some embodiments, prediction component 34 may be configured to continuously receive, during at least a part of the sleep session, the other samples to predict sleep stages of the subject occurring around other times that are subsequent to the other samples being respectively provided to the prediction component. The samples may be received from the sampling component 30.

In some embodiments, prediction component 34 may be configured to predict one or more sleep states based on information from subjects having one or more similarities with subject 12 (e.g., similar brain activity information, demographic information, vital sign information, medical/health condition information, treatment hi story information, similar desired outcome (e.g., from sensory simulation), similar sleep information, and/or other similarities with subject 12.)

In some embodiments, prediction component 34 may include a prediction model configured to determine a probability of the sleep state that may occur around the second time. In some embodiments, the prediction model may be configured to provide one or more probabilities of individual ones of the sleep sates occurring at or around the second time (e.g., wakefulness, REM sleep, stage N1, stage N2, and/or stage N3 sleep). In some embodiments, perdition model (and/or prediction component 34) may be configured to determine the (future) sleep state of the subject based on the one or more probabilities of individual ones of the sleep sates that may occur around the second time. For example, in some embodiments, prediction component 34 may determine that the sleep state with the higher probability value is the sleep state that may occur at the second time. The prediction models may include one or more neural networks (e.g., deep neural networks, artificial neural networks, or other neural networks), other machine learning models, or other prediction models. As an example, the neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections may be enforcing or inhibitory, in their effect on the activation state of connected neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free-flowing, with connections interacting in a more chaotic and complex fashion.

In some embodiments, the prediction model may be a deep neural network. Machine learning in the form of deep neural networks that take advantage of large volumes of data to automatically derive features and build highly performant classifiers with significantly higher accuracies compared to other feature based approaches. Using a large database (e.g., of EEG sleep data, or other sleep data) a deep learning classifier may be built to predict sleep states with a prediction horizon in the order of minutes. In some embodiments, the deep neural network operation may include a set of algorithms that attempt to model high-level abstractions in data by using a deep graph with multiple processing layers, composed of multiple linear and/or non-linear transformations. For example, the deep neural network may include an architecture composed of convolutional layers (e.g., filters). In some embodiments, the prediction model may include recurrent layers. In some embodiments, the recurrent layers may be implemented as long-short term memory elements that provide the network with the memory to use past decisions to refine prediction accuracy. In some embodiments, use of neural networks may be advantageous because they can produce their predictions in terms of probabilities associated with pre-defined sleep stages (e.g. Wake, REM, N1, N2, N3 sleep). In some embodiments, the set of probabilities constitute a "soft decision" vector, which can be translated into a "hard decision" by associating a sleep stage prediction to the highest probability. In some embodiments, the soft decision makes it possible to consider sleep states that are mapped into a continuum as opposed to sleep stages, which are in a discrete space.

FIG. 3 illustrates example operations 300 performed by system 10 configured to predict sleep states, in accordance with one or more embodiments. In some embodiments, system 10 may be in the form of wearable headband 301. In some embodiments, some or all components of system 10 may be included in wearable headband 301. In some embodiments, some or all components of system 10 may be included in any type of wearable device as described above (not shown here). The brain activity during sleep is monitored in real-time using the electroencephalogram (EEG) 302. At time "t−τ" 304 a window 306 with "W" samples is fed to a prediction model 308 which has the ability to predict 309 the sleep state at time "t" 310. The prediction model may include convolutional layers 311 (which can be thought of as filters) and recurrent layers 312 (which without loss of generality can be implemented as long-short term memory elements) that allow the network with state memory to use past decisions to refine prediction accuracy. At time "t" 310, the processing leading to the intervention during sleep considers first whether the intervention is likely to disturb sleep 314 (which can be accomplished by quantifying the high frequency content in the EEG). The quantification of the risk of disturbing sleep does also benefit from the prediction model. If the risk of disturbing sleep is sufficiently low 316, the next step consists in detecting the current sleep state 318. The current sleep state 318 is combined with the prediction 310 at 319 that the prediction model produced at time "t−τ" (i.e. τ units of time ago) to decide whether the intervention should happen 320. The settings (parameters of the intervention) may be decided taking into account the prediction. The settings may be stored in data storage 322. If it has been decided to intervene 324, stimulation is delivered 324 to subject 12.

In some embodiments, prediction model (e.g., a deep neural network or other machine learning model) may use structured and/or unstructured data for learning. In some embodiments, data may include data received from sensor(s) 18. For example, one or more images, symbols, video, audio, text, and/or other structured data. In some embodiments, learning can be supervised or unsupervised.

Figure 4:
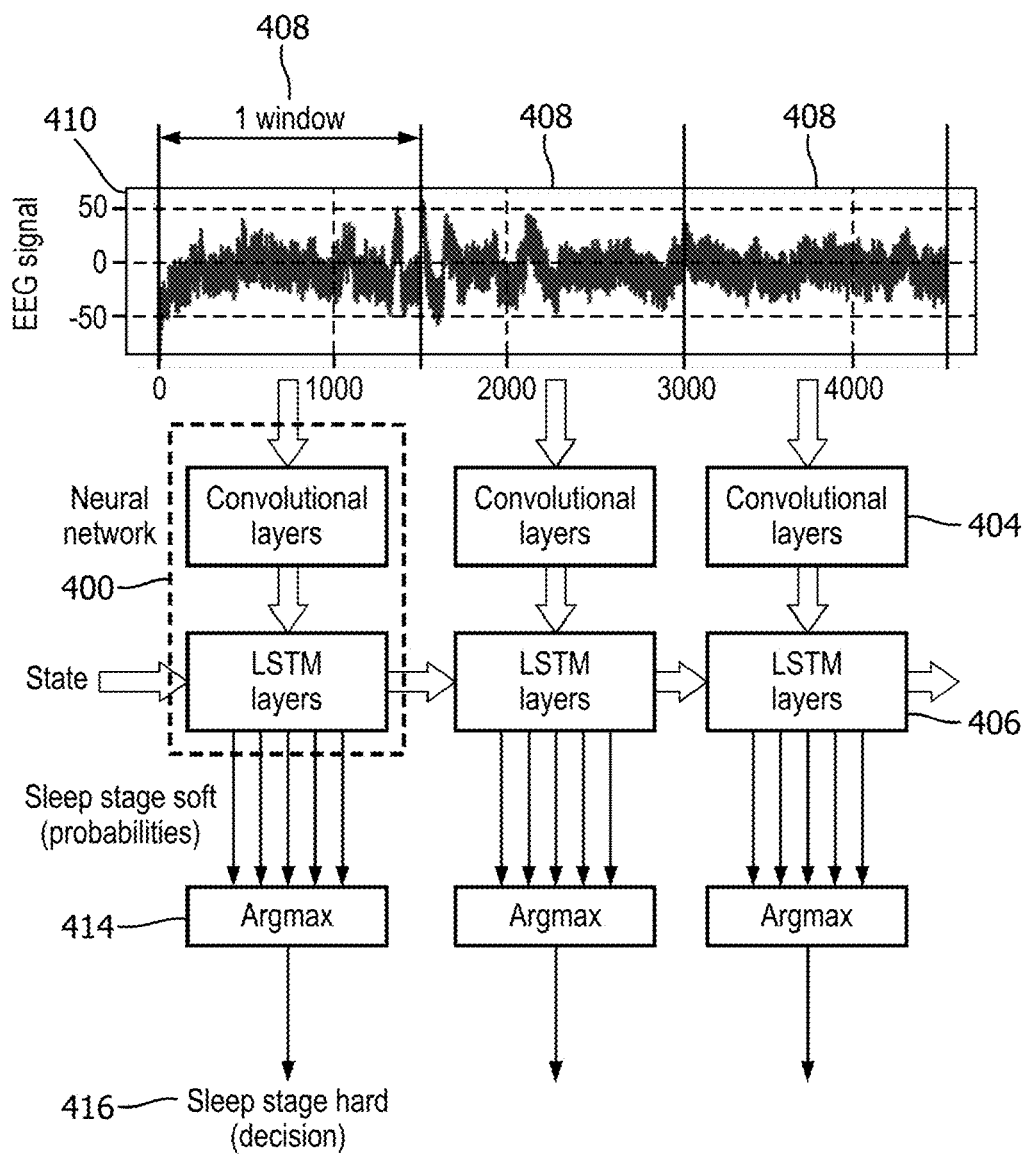
FIG. 4 illustrates an example of a prediction model, in accordance with one or more embodiments.

In some embodiments, the prediction model is a convolution neural network (CNN) & long short-term memory (LSTM). In some embodiments, the neural network can consist of dense layers, convolutional layers, recurrent layers or combinations thereof. In some embodiments, the raw EEG signal (or other output signals as described above) may be windowed, possibly with overlap, and applied to the input of a neural network. The final output of the network are soft probability values for each sleep stage class for each applied window. In some embodiments, these probability values may be transformed via an ARGMAX operator into a hard decision sleep stage value for each window. FIG. 4 illustrates an example of a prediction model, in accordance with one or more embodiments. The prediction model 400 is a convolution neural network (CNN) including convolutional layers 404, and long short-term memory (LSTM) including LSTM layers 406. Prediction model 400 is displayed temporally "unrolled" for three consecutive windows 408. EEG signal 410 is windowed and applied to the input of a neural network 402. The final output of the network are soft probability values 412 for each sleep stage class for each applied window. In some embodiments, these probability values may be transformed via an ARGMAX operator 414 into a hard decision sleep stage value 416 for each window.

Figure 5:
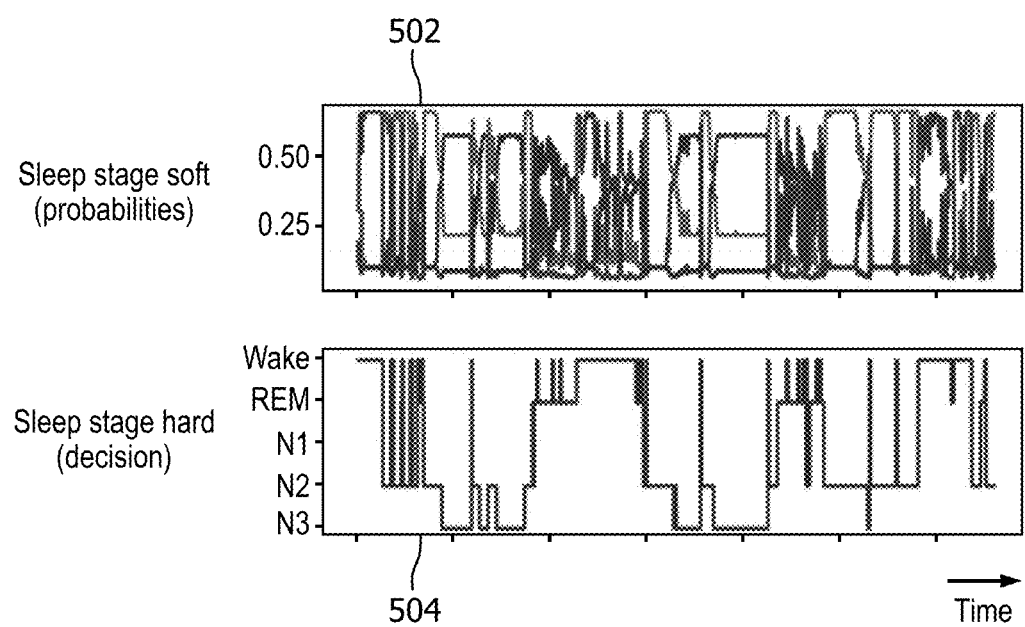
FIG. 5 illustrates an example of a sample output signals, in accordance with one or more embodiments.

FIG. 5 illustrates an example of a sample output signals, in accordance with one or more embodiments. Diagram 502 represents a detailed view of the soft probabilities for each stage (as described above with respect to FIG. 4). Different stages are represented with different colors (purple, green, orange, blue, and red. Diagram 504 represents the hard decision sleep stage.

Figure 6:
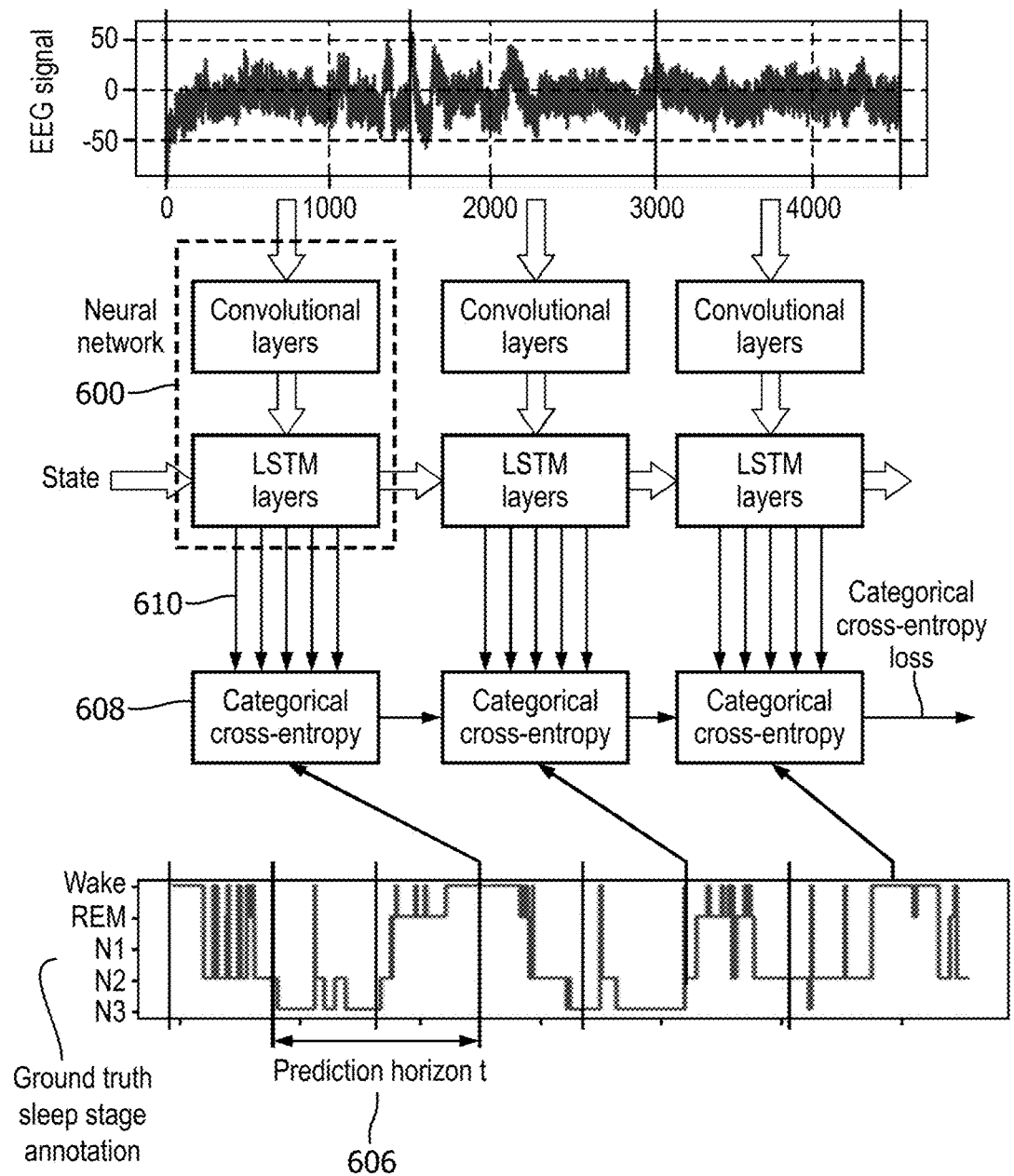
FIG. 6 illustrates an example of a prediction model and inputs/outputs to and from the prediction model, in accordance with one or more embodiments.

FIG. 6 illustrates an example of prediction model 600 and inputs/outputs to and from prediction model 600, in accordance with one or more embodiments. As an example, prediction model 600 (e.g., a neural network or other machine learning model) may include one or more convolutional layers, long short-term memory layers, or other components). In one use case, during training of prediction model 600, sleep stage targets are applied with a forward shift. This is expected to provide prediction model 600 with a more accurate predictive behavior. In some embodiments, a prediction horizon of κ (=1) windows 606 has been chosen for illustration. Longer prediction horizons are possible. Categorical cross entropy 608 is applied to the soft probabilities 610 to determine value to the sleep state at the time of prediction κ (=1).

Figure 7:
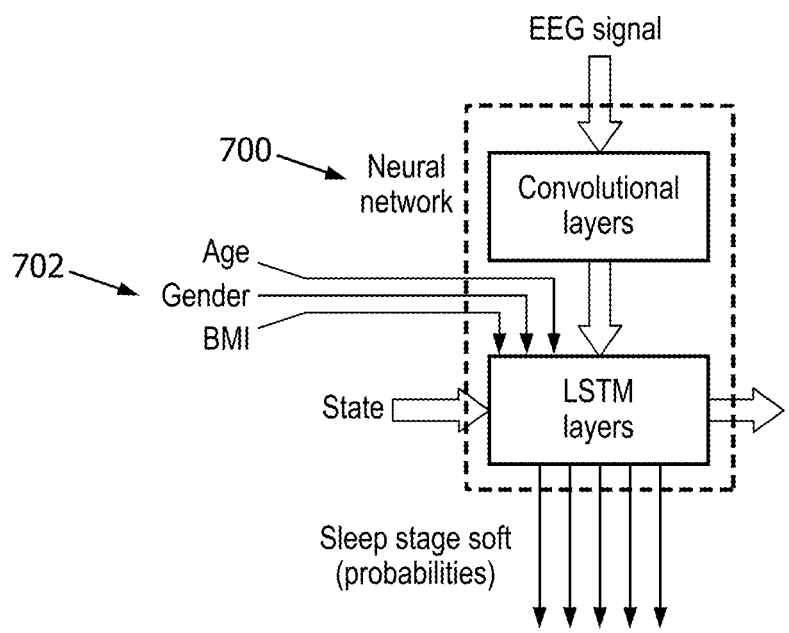
FIG. 7 illustrates an example of prediction model, in accordance with one or more embodiments.

In some embodiments, to improve performance of prediction model 600, subject-specific information may be applied during use (e.g., the user's age, gender, BMI, or other subject information). In some embodiments, during the neural network training, subject information may be applied with each EEG training example. In some embodiments, subject information distributions of the training data set should roughly match the distributions of the intended target user group (e.g., prediction model 600 is trained using the subject-specific data, data from other subjects with one or more similarities with the subject, or other data). FIG. 7 illustrates an example of prediction model 700, in accordance with one or more embodiments where subject information 702 is applied to neural network 704 to improve performance of the prediction model.

Returning to FIG. 1, risk component 36 may be configured to determine stimulation information to be delivered to the subject at a given time (or before, or around the given time). In some embodiments, risk component 36 may be configured to determine stimulation information to be delivered to the subject without causing a sleep disturbance (e.g., causing arousals, or causing the subject to feel the stimulation, or remember the stimulation after he wakes up, etc.). In some embodiments, the stimulation information indicates one or more stimulator parameters related to stimulation. For example, type of stimulation, duration, time interval between the stimulations, intensity of the stimulations, volume of the stimulations, frequency, and/or other parameters of the stimulator(s). In some embodiments, stimulation information may be obtained from one or more components within or outside system 10. In some embodiments, stimulation information may be provided by a user (healthcare provider, a caretaker, a nurse, etc.), the subject, manufacturer, etc. In some embodiments, stimulation information may be dynamically obtained (or determined) during the sleep session. For example, based on the detected or predicted sleep states (e.g., one or more parameters of the stimulation information may change or be adjusted dynamically based on the detected or predicted sleep states.) In some embodiments, stimulation information may be obtained (or determined) prior to the second time, based on the prediction of the sleep stage at the second time. In some embodiments, the stimulation information may be continuously determined based on the predictions of the sleep states during parts of (or the whole) sleep session.

In some embodiments, risk component 36 may be configured to determine a sleep disturbance risk of providing the stimulation at a given time (or before, or around the given time). For example, in some embodiments, sleep disturbance risk may be determined by quantifying the high frequency content in the EEG. In some embodiments, sleep disturbance risk may be determined based on the detected and/or the predicted sleep states. In some embodiments, the sleep disturbance risk may be determined based on historical data from the subject, or other subjects. For example, a sleep disturbance risk may be higher in cases where the detected or predicted sleep state had caused sleep disturbance for the subject of for other subjects in the past. In some embodiments, a sleep disturbance risk may be low in cases where the detected or predicted sleep state had caused no or little sleep disturbance for the subject of for other subjects in the past. For example, in the case the detected or predicted sleep state is non-REM sleep stage 2, the sleep disturbance risk may be low. In some embodiments, one or more risk criteria may be determined. In some embodiments, the one or more risk criteria may include one or more thresholds. For example an upper risk threshold and a lower risk threshold. In some embodiments, the upper risk threshold indicates that the stimulation will most likely cause sleep disturbance when the disturbance risk reaches, breaches, or is around the upper risk threshold. In some embodiments, a lower risk threshold indicates that the stimulation will most likely not cause sleep disturbance when the disturbance risk reaches, breaches, or is around the lower risk threshold. The risk criteria may be determined by risk component 36, prediction component 34, a user, the subject or other components within or outside of system 10.

In some embodiments, the sleep disturbance risk may be determined by prediction component 34 (or other components of system 10). In some embodiments, sleep disturbance risk may be determined in the form of a probability (or a set of probabilities). For example, prediction component 34 may be configured to predict sleep state for a given time (or, before, or around the given time) along with determining one or more parameters of stimulation to be given to the subject, and along with a sleep disturbance risk of the one or more parameters of stimulation. In some embodiments, sleep disturbance risk may be determined (or assessed) by a machine learning model.

Control component 38 is configured to control stimulator(s) 16 to provide stimulation to subject 12. In some embodiments, control component may be configured to cause stimulator(s) 16 to provide stimulation, based on the stimulation information, the detected and/or predicted sleep state, the sleep disturbance risk, and/or to the subject information at a given time (or around the given time) during the sleep session. Control component 38 may be configured to control stimulator(s) 16 to provide stimulation to subject 12 prior to a sleep session, during a current sleep session, after a sleep session, and/or at other times. Control component 38 may be configured to control stimulator(s) 16 to provide stimulation during specific sleep states and/or sleep stages. For example, stimulator(s) 16 may be configured to provide stimulation to subject 12 during slow wave sleep in a sleep session. In some embodiments, control component 38 may be configured to control stimulator(s) 16 to provide stimulation at a timing of slow waves based on the detected or predicted individual slow waves.

In some embodiments, control component 38 may be configured to cause stimulators 16 to provide the stimulation to the subject around a given time of the sleep session based on the determination that the sleep disturbance risk does not satisfy the predetermined risk criteria (e.g., the upper threshold). In some embodiments, control component 38 may be configured to stop (or decrease stimulation) stimulators 16 from providing the stimulation to the subject around a given time of the sleep session based on the determination that the sleep disturbance risk satisfies the predetermined risk criteria (e.g., the upper threshold).

In some embodiments, control component 38 may be configured to control stimulator(s) 16 to adjust the stimulation based on the stimulation information, the detected and/or predicted sleep state, the sleep disturbance risk, and/or to the subject information at a given time (or around the given time) during the sleep session. Stimulation may be adjusted between an upper threshold and a lower threshold. The upper thresholds and a lower thresholds may be determined based on subject 12, and/or based on other parameters determined by a user (e.g., healthcare professional, caregiver, etc.), and/or one or more components within or outside of system 10. In some embodiments, system 10 may be configured to adjust one or more parameters of the stimulation (e.g., type of stimulation, time interval, intensity, volume, frequency, etc.).

In some embodiments, as shown in FIG. 1, system 10 may include one or more of external resources 14, electronic storage 22, client computing platform(s) 24, network 26, and/or other components, all being communicatively coupled via a network 26.

External resources 14 include sources of patient and/or other information. In some embodiments, external resources 14 include sources of patient and/or other information, such as databases, websites, etc., external entities participating with system 10 (e.g., a medical records system of a healthcare provider that stores medical history information for populations of patients), one or more servers outside of system 10, a network (e.g., the internet), electronic storage, equipment related to Wi-Fi technology, equipment related to Bluetooth® technology, data entry devices, sensors, scanners, and/or other resources. In some embodiments, some or all of the functionality attributed herein to external resources 14 may be provided by resources included in system 10. External resources 14 may be configured to communicate with processor 20, computing devices 24, electronic storage 22, and/or other components of system 10 via wired and/or wireless connections, via a network (e.g., a local area network and/or the internet), via cellular technology, via Wi-Fi technology, and/or via other resources.

Electronic storage 22 includes electronic storage media that electronically stores information. The electronic storage media of electronic storage 22 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may be (in whole or in part) a separate component within system 10, or electronic storage 22 may be provided (in whole or in part) integrally with one or more other components of system 10 (e.g., computing devices 18, processor 20, etc.). In some embodiments, electronic storage 22 may be located in a server together with processor 20, in a server that is part of external resources 14, in a computing device 24, and/or in other locations. Electronic storage 22 may include one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via a computing device 24 and/or graphical user interface 40 and/or other external computing systems, information received from external resources 14, stimulators 16, sensors 18, and/or other information that enables system 10 to function as described herein.

Client computing platform(s) 24 is configured to provide an interface between system 10 and subject 12, and/or other users through which subject 12 and/or other users may provide information to and receive information from system 10. For example, client computing platform(s) 24 may display a representation of the output signal from sensors 18 (e.g., an EEG, 2D/3D images, video, audio, text, etc.) to a user. This enables data, cues, results, instructions, and/or any other communicable items, collectively referred to as "information," to be communicated between a user (e.g., subject 12, a doctor, a caregiver, and/or other users) and one or more of stimulator(s) 16, processor 20, electronic storage 22, and/or other components of system 10.

Examples of interface devices suitable for inclusion in client computing platform(s) 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, client computing platform(s) 24 comprises a plurality of separate interfaces. In some embodiments, client computing platform(s) 24 comprises at least one interface that is provided integrally with processor 20, stimulator(s) 16, sensor(s) 18, and/or other components of system 10. Computing devices 24 are configured to provide interfaces between caregivers (e.g., doctors, nurses, friends, family members, etc.), patients, and/or other users, and system 10. In some embodiments, individual computing devices 24 are, and/or are included, in desktop computers, laptop computers, tablet computers, smartphones, and/or other computing devices associated with individual caregivers, patients, and/or other users. In some embodiments, individual computing devices 24 are, and/or are included, in equipment used in hospitals, doctor's offices, and/or other medical facilities to patients; test equipment; equipment for treating patients; data entry equipment; and/or other devices. Computing devices 24 are configured to provide information to, and/or receive information from, the caregivers, patients, and/or other users. For example, computing devices 24 are configured to present a graphical user interface 40 to the caregivers to facilitate display representations of the data analysis, and/or other information. In some embodiments, graphical user interface 40 includes a plurality of separate interfaces associated with computing devices 24, processor 20 and/or other components of system 10; multiple views and/or fields configured to convey information to and/or receive information from caregivers, patients, and/or other users; and/or other interfaces.

In some embodiments, computing devices 24 are configured to provide graphical user interface 40, processing capabilities, databases, and/or electronic storage to system 10. As such, computing devices 24 may include processors 20, electronic storage 22, external resources 14, and/or other components of system 10. In some embodiments, computing devices 24 are connected to a network (e.g., the internet). In some embodiments, computing devices 24 do not include processors 20, electronic storage 22, external resources 14, and/or other components of system 10, but instead communicate with these components via the network. The connection to the network may be wireless or wired. For example, processor 20 may be located in a remote server and may wirelessly cause display of graphical user interface 40 to the caregivers on computing devices 24. As described above, in some embodiments, an individual computing device 18 is a laptop, a personal computer, a smartphone, a tablet computer, and/or other computing devices. Examples of interface devices suitable for inclusion in an individual computing device 18 include a touch screen, a keypad, touch-sensitive and/or physical buttons, switches, a keyboard, knobs, levers, a display, speakers, a microphone, an indicator light, an audible alarm, a printer, and/or other interface devices. The present disclosure also contemplates that an individual computing device 18 includes a removable storage interface. In this example, information may be loaded into a computing device 18 from removable storage (e.g., a smart card, a flash drive, a removable disk, etc.) that enables the caregivers, patients, and/or other users to customize the implementation of computing devices 24. Other exemplary input devices and techniques adapted for use with computing devices 24 include, but are not limited to, an RS-232 port, an RF link, an IR link, a modem (telephone, cable, etc.), and/or other devices.

The network 26 may include the Internet and/or other networks, such as local area networks, cellular networks, Intranets, near field communication, frequency (RF) link, Bluetooth™, Wi-Fi™, and/or any type(s) of wired or wireless network(s). Such examples are not intended to be limiting, and the scope of this disclosure includes embodiments in which external resources 14, stimulator(s) 16, sensor(s) 18, processor(s) 20, electronic storage 22, and/or client computing platform(s) 24 are operatively linked via some other communication media.

Figure 8:
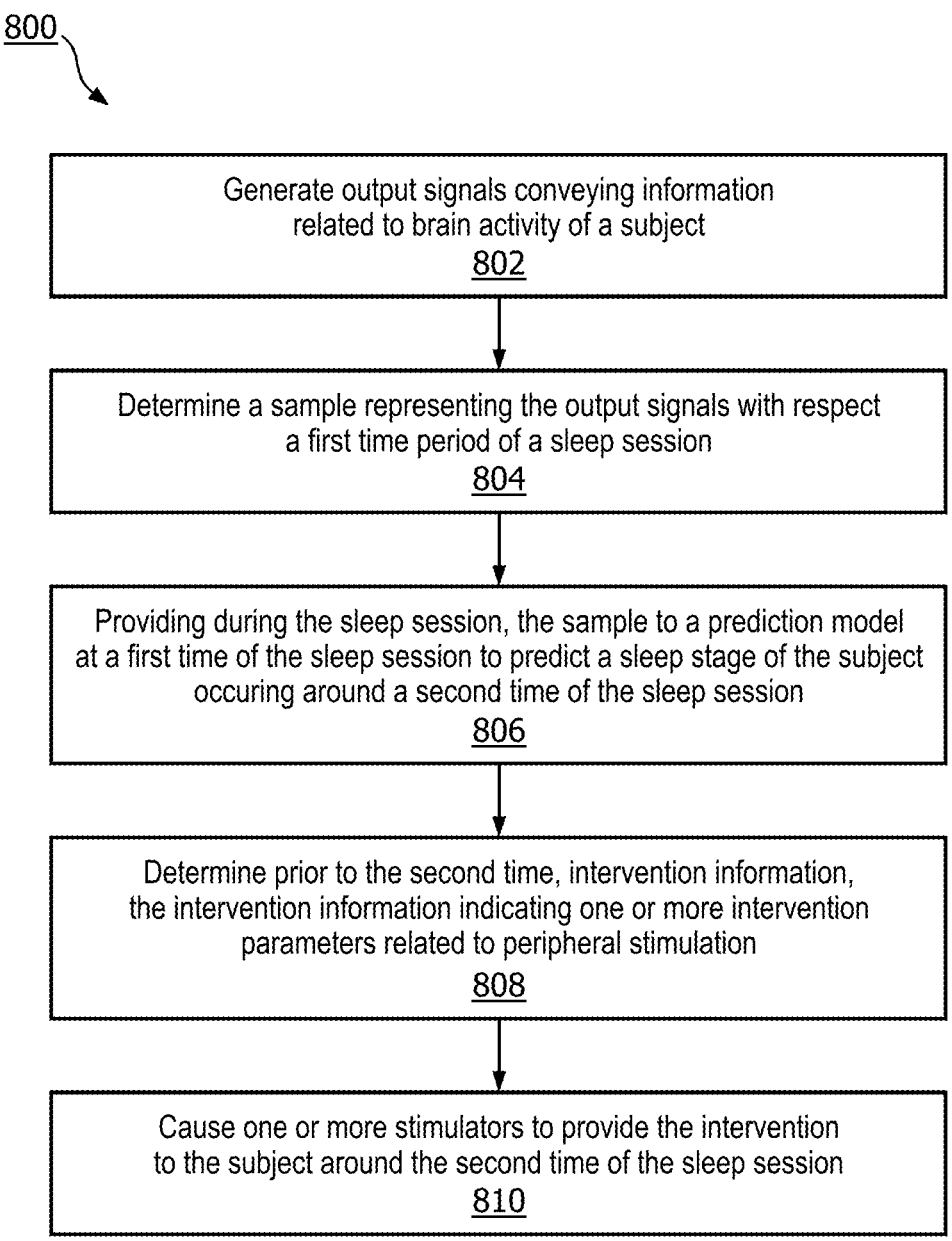
FIG. 8 illustrates a method for prediction of a sleep stage and intervention preparation in advance of the sleep stage's occurrence, in accordance with one or more embodiments.

FIG. 8 illustrates a method 800 for facilitating prediction of a sleep stage and intervention preparation in advance of the sleep stage's occurrence. The system comprises one or more sensors, one or more physical computer processors, and/or other components. The one or more processors are configured to execute one or more computer program components. The one or more computer program components may comprise a subject information component 28, a sampling component 30, a detection component 32, a prediction component 34, a risk component 36, a control component 38, and/or other components. The operations of method 800 presented below are intended to be illustrative. In some embodiments, method 800 may be accomplished with one or more additional operations not described, and/or without one or more of the operations discussed. Additionally, the order in which the operations of method 800 are illustrated in FIG. 8 and described below is not intended to be limiting.

In some embodiments, method 800 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 800 in response to instructions stored electronically on an electronic storage medium. The one or more processing devices may include one or more devices configured through hardware, firmware, and/or software to be specifically designed for execution of one or more of the operations of method 800.

At an operation 802, output signals conveying information related to brain activity of the subject during a sleep session are generated. In some embodiments, operation 802 is performed by one or more sensors the same as or similar to sensors 18 (shown in FIG. 1 and described herein).

At an operation 804, determine a sample representing the output signals with respect a first time period of a sleep session. In some embodiments, operation 804 is performed by a computer processor component the same as or similar to sampling component 30 (shown in FIG. 1 and described herein).

At an operation 806, provide, during the sleep session, the sample to a prediction model at a first time of the sleep session to predict a sleep stage of the subject occurring around a second time of the sleep session. In some embodiments, operation 806 is performed by a computer processor component the same as or similar to a prediction component 34 (shown in FIG. 1 and described herein).

At an operation 808, determine, prior to the second time, stimulation information based on the prediction of the sleep stage, the stimulation information indicating one or more stimulator parameters related to peripheral stimulation. In some embodiments, operation 808 is performed by a computer processor component the same as or similar to, a risk component 36 (shown in FIG. 1 and described herein).

At an operation 810, cause, based on the stimulation information, one or more stimulators (16) to provide the intervention to the subject around the second time of the sleep session. In some embodiments, operation 810 is performed by a computer processor component the same as or similar to control component 38 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A wearable device configured to facilitate prediction of a sleep stage and intervention preparation in advance of the sleep stage's occurrence, the wearable device comprising:
    one or more sensors configured to be placed on a subject and to generate output signals conveying information related to brain activity of the subject;
    one or more stimulators configured to provide an intervention to the subject; and
    one or more physical processors configured by computer-readable instructions to:
        determine a sample representing the output signals with respect to a first time period of a sleep session;
        provide, during the sleep session, the sample to a prediction model at a first time of the sleep session to predict the sleep stage of the subject occurring at a second future time of the sleep session;
        determine, prior to the second future time, intervention information based on the prediction of the sleep stage, the intervention information indicating one or more stimulator parameters related to peripheral stimulation; and
        cause, based on the intervention information, the one or more stimulators to provide the intervention to the subject at the second future time of the sleep session,
    wherein the one or more physical processors are further configured to:
        determine a sleep disturbance risk of providing the intervention at the second future time to the subject;
        determine whether the sleep disturbance risk satisfies a predetermined risk criteria; and
        cause the one or more stimulators to provide the intervention to the subject at the second future time of the sleep session based on the intervention information if it is determined that the sleep disturbance risk does not satisfy the predetermined risk criteria, and to cause the one or more stimulators to decrease the intervention to the subject at the second future time of the sleep session if it is determined that the sleep disturbance risk does satisfy the predetermined risk criteria.

2. The wearable device of claim 1, wherein the one or more physical processors are configured to obtain the prediction of the sleep stage from the prediction model.

3. The wearable device of claim 1, wherein the one or more physical processors are configured to:
    obtain, from the prediction model, a probability of the sleep stage occurring at the second future time and one or more other probabilities of one or more other sleep stages occurring at the second future time; and
    selecting, based on the probability and the one or more other probabilities, the sleep stage to obtain the prediction of the sleep stage.

4. The wearable device of claim 1, wherein the second future time of the sleep session is at least ten seconds after the first time of the sleep session.

5. The wearable device of claim 1, wherein the one or more processors are further configured to:
continuously determine, during at least a part of the sleep session, other samples representing the output signals with respect to one or more other time periods of the sleep session;
continuously provide, during at least a part of the sleep session, the other samples to the prediction model to predict sleep stages of the subject occurring at other times that are subsequent to the other samples being respectively provided to the prediction model; and
continuously determine, during at least a part of the sleep session, further intervention information based on the predictions of the sleep stages.

6. The wearable device of claim 1, wherein the one or more processors are further configured to:
obtain historical information related to one or more previous sleep sessions or biographical information related to the subject; and
provide the historical data or biographical information to the prediction model to cause the prediction model to generate one or more outputs related to the prediction of the sleep stage based on the historical data or the biographical information.

7. The wearable device of claim 1, wherein the intervention comprises magnetic stimulation, auditory stimulation, light stimulation, electrical stimulation, haptic stimulation, or olfactory stimulation.

8. A method for facilitating prediction of a sleep stage and intervention preparation in advance of the sleep stage's occurrence, the method comprising:
generating, with one or more sensors, output signals conveying information related to brain activity of a subject;
determining, with one or more physical processors, a sample representing the output signals with respect to a first time period of a sleep session;
providing, with the one or more physical processors, during the sleep session, the sample to a prediction model at a first time of the sleep session to predict the sleep stage of the subject occurring at a second future time of the sleep session;
determining, with the one or more physical processors, prior to the second future time, intervention information based on the prediction of the sleep stage, the intervention information indicating one or more stimulator parameters related to peripheral stimulation; and
causing, with the one or more physical processors, based on the intervention information, one or more stimulators to provide the intervention to the subject at the second future time of the sleep session;
providing, with one or more stimulators, the intervention to the subject,
determining, with the one or more physical processors, a sleep disturbance risk of providing the intervention at the second future time to the subject;
determining, with the one or more physical processors, whether the sleep disturbance risk satisfies a predetermined risk criteria; and
causing, with the one or more physical processors, the one or more stimulators to provide the intervention to the subject at the second future time of the sleep session based on the intervention information if it is determined that the sleep disturbance risk does not satisfy the predetermined risk criteria, and causing the one or more stimulators to decrease the intervention to the subject at the second future time of the sleep session if it is determined that the sleep disturbance risk does satisfy the predetermined risk criteria.

9. The method of claim 8, further comprising obtaining the prediction of the sleep stage from the prediction model.

10. The method of claim 8, further comprising:
obtaining, with the one or more physical processors, from the prediction model, a probability of the sleep stage occurring at the second future time and one or more other probabilities of one or more other sleep stages occurring at the second future time; and
selecting, with the one or more physical processors, based on the probability and the one or more other probabilities, the sleep stage to obtain the prediction of the sleep stage.

11. The method of claim 8, wherein the second future time of the sleep session is at least ten seconds after the first time of the sleep session.

12. The method of claim 8, further comprising:
continuously determining, with the one or more physical processors, during at least a part of the sleep session, other samples representing the output signals with respect to one or more other time periods of the sleep session;
continuously providing, with the one or more physical processors, during at least a part of the sleep session, the other samples to the prediction model to predict sleep stages of the subject occurring at other times that are subsequent to the other samples being respectively provided to the prediction model; and
continuously determining, with the one or more physical processors, during at least a part of the sleep session, further intervention information based on the predictions of the sleep stages.

13. The method of claim 8, further comprising:
obtaining, with the one or more physical processors, historical information related to one or more previous sleep sessions or biographical information related to the subject; and
providing, with the one or more physical processors, the historical data or biographical information to the prediction model to cause the prediction model to generate one or more outputs related to the prediction of the sleep stage based on the historical data or the biographical information.

14. The method of claim 8, wherein the intervention comprises magnetic stimulation, auditory stimulation, light stimulation, electrical stimulation, haptic stimulation, or olfactory stimulation.

15. A system configured to facilitate prediction of a sleep stage and intervention preparation in advance of the sleep stage's occurrence, the system comprising:
means for generating output signals conveying information related to brain activity of a subject;
one or more stimulators configured to provide an intervention to the subject; and
means for determining a sample representing the output signals with respect to a first time period of a sleep session;
means for providing, during the sleep session, the sample to a prediction model at a first time of the sleep session to predict the sleep stage of the subject occurring at a second future time of the sleep session;
means for determining, prior to the second future time, intervention information based on the prediction of the sleep stage, the intervention information indicating one or more stimulator parameters related to peripheral stimulation; and means for causing, based on the intervention information, the one or more stimulators to provide the intervention to the subject at the second future time of the sleep session;

wherein the means for determining are further configured to:
  determine a sleep disturbance risk of providing the intervention at the second future time to the subject; and
  determine whether the sleep disturbance risk satisfies a predetermined risk criteria;

wherein the means for causing are further configured to:
  cause the one or more stimulators to provide the intervention to the subject at the second future time of the sleep session based on the intervention information if it is determined that the sleep disturbance risk does not satisfy the predetermined risk criteria, and to cause the one or more stimulators to decrease the intervention to the subject at the second future time of the sleep session if it is determined that the sleep disturbance risk does satisfy the predetermined risk criteria.

16. The system of claim 15, further comprising means for obtaining the prediction of the sleep stage from the prediction model.

17. The system of claim 15, further comprising:
  means for obtaining, from the prediction model, a probability of the sleep stage occurring at the second future time and one or more other probabilities of one or more other sleep stages occurring at the second future time; and
  means for selecting, based on the probability and the one or more other probabilities, the sleep stage to obtain the prediction of the sleep stage.

18. The system of claim 15, wherein the second future time of the sleep session is at least ten seconds after the first time of the sleep session.

* * * * *